(12) United States Patent
Christenson et al.

(10) Patent No.: US 12,029,664 B2
(45) Date of Patent: Jul. 9, 2024

(54) PROSTHETIC ATTACHMENT DEVICE FOR OSSEOINTEGRATED IMPLANTS

(71) Applicant: Motion Control, Inc., Salt Lake City, UT (US)

(72) Inventors: Jeffery David Christenson, West Valley City, UT (US); Edwin Kay Iversen, Salt Lake City, UT (US); Kent Nelson Bachus, Salt Lake City, UT (US); Heath Byron Henninger, Salt Lake City, UT (US); Alex Drew, Austin, TX (US)

(73) Assignee: Motion Control, Inc., Salt Lake City, UT (US)

( * ) Notice: Subject to any disclaimer, the term of this patent is extended or adjusted under 35 U.S.C. 154(b) by 31 days.

(21) Appl. No.: 17/740,239

(22) Filed: May 9, 2022

(65) Prior Publication Data
US 2022/0354671 A1   Nov. 10, 2022

Related U.S. Application Data

(60) Provisional application No. 63/185,810, filed on May 7, 2021.

(51) Int. Cl.
*A61F 2/78* (2006.01)

(52) U.S. Cl.
CPC ........ *A61F 2/78* (2013.01); *A61F 2002/7887* (2013.01)

(58) Field of Classification Search
CPC ........................... A61F 2/78; A61F 2002/7887
See application file for complete search history.

(56) References Cited

U.S. PATENT DOCUMENTS

| | | | |
|---|---|---|---|
| 10,369,028 B2 * | 8/2019 | Kuiken | A61F 2/78 |
| 2008/0058957 A1 * | 3/2008 | Newcombe | A61F 2/78 623/32 |
| 2019/0175370 A1 * | 6/2019 | Christenson | A61F 2/76 |
| 2020/0368042 A1 * | 11/2020 | Porter | A61F 2/78 |

* cited by examiner

*Primary Examiner* — Bruce E Snow
(74) *Attorney, Agent, or Firm* — Foley & Lardner LLP

(57) ABSTRACT

Technology is described which can provide a quick disconnect and overload protection mechanism for a prosthetic limb that is used with an osseointegrated percutaneous post. The technology can provide a way to easily don and doff a prosthetic limb. This quick disconnect may also provide a resettable torsional overload protection mechanism and/or a fusible link that may act to protect the osseointegrated percutaneous post from both axial and bending over-loads.

16 Claims, 6 Drawing Sheets

PROSTHETIC ATTACHMENT DEVICE FOR OSSEOINTEGRATED IMPLANTS

PRIORITY DATA

This application claims the benefit of U.S. Provisional Patent Application Ser. No. 63/185,810, filed May 7, 2021, which is incorporated herein by reference.

BACKGROUND

Prostheses (or prosthetics) are artificial devices that replace human body parts (e.g., fingers, hands, arms, legs). Generally, prostheses may be used to replace human body parts lost by injury or missing from birth. Prostheses are typically connected to a person's body using a socket that can receive a remnant limb.

Prostheses can also be connected to a person's body using an osseointegrated implant where a metal implant may be used which is implanted into the bone of the remnant limb and passes through the skin to the outside of a person's body. A percutaneous post may be implanted (osseointegrated) into the remnant limb of an individual with limb-loss, and the percutaneous post is used to attach a prosthesis to the amputee's remnant limb. In some situations, a porous titanium coating on the implant is used to enable a person's skin and bone to connect into the implant and secure the osseointegrated implant or percutaneous post.

DETAILED DESCRIPTION

Figure 1A:
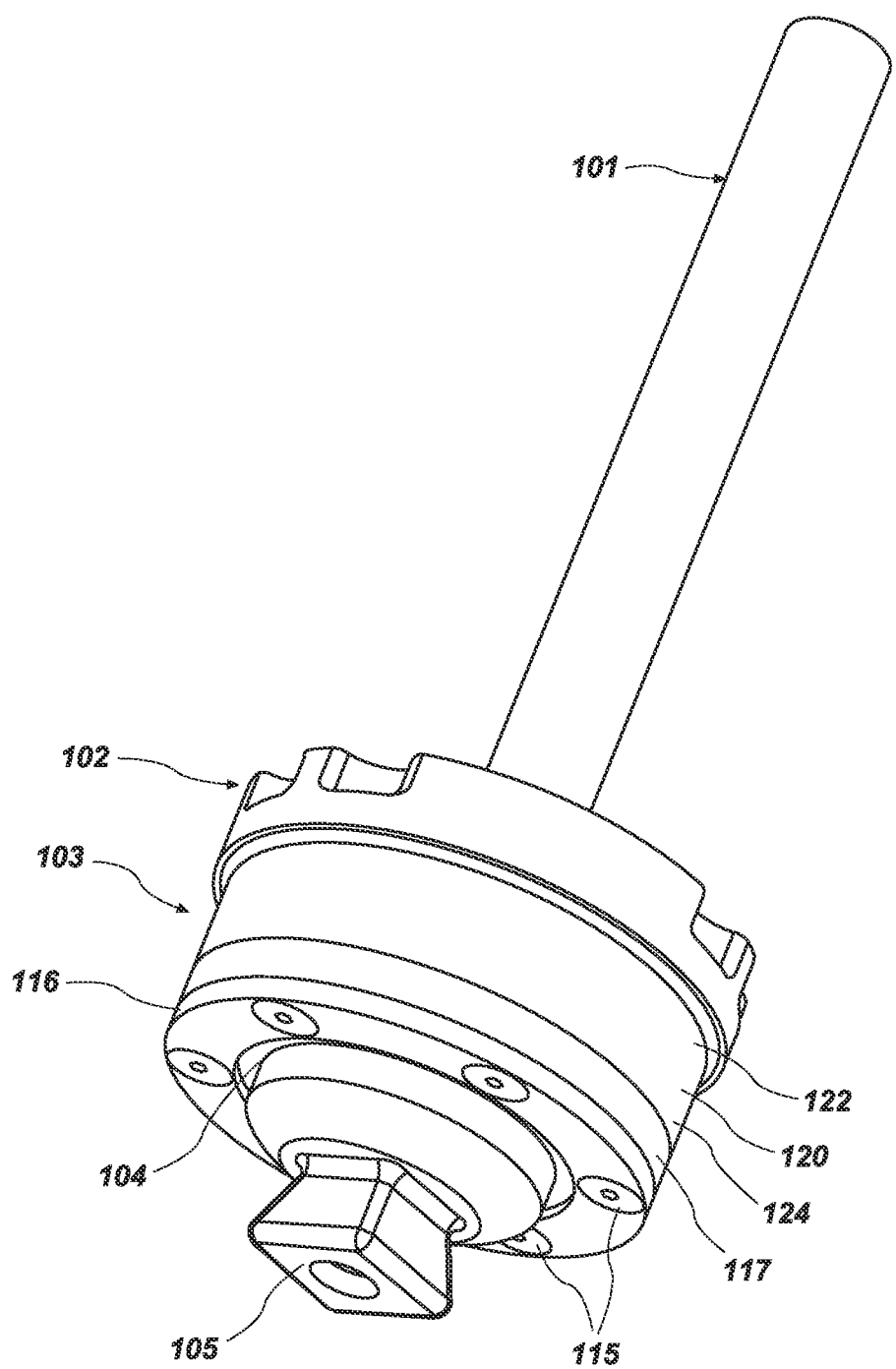
FIG. 1A is an isometric side view of an example of a quick-disconnect and overload protection device for prosthesis users.

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

A technology is described which can provide a quick disconnect and overload protection mechanism for a prosthetic limb that is used with an osseointegrated percutaneous post. The technology may enable a user to easily don and doff a prosthetic limb. This overload protection device may also provide a resettable torsional overload protection mechanism and a fusible link which is "drum-like". The fusible link may act to protect the osseointegrated percutaneous post from both axial and bending over-loads.

FIG. 1A illustrates an isometric view of an example of the quick-disconnect and overload protection device. A percutaneous post support and quick disconnect assembly with a cap 102 may be provided to allow the percutaneous post 101 to be inserted into and supported by the quick disconnect assembly. A torsional resettable overload mechanism 103 with a housing 120 having a first end 122 and a second end 124 is included to provide torsional breakaway capability in order protect the prosthesis use from torsional forces. A fusible link 104 is provided for axial and bending overload protection.

FIG. 1A further illustrates that the example assembly may provide a quick disconnect for donning and doffing of the prosthesis from the osseointegrated percutaneous post. This example device or system allows the prosthesis user to remove the prosthesis easily by rotating a cap 102 counter clockwise and locking the cap 102 in place by rotating the cap 102 clockwise.

In one configuration, the percutaneous post support may be a permanent post support for the overload support device and may be fasteners such as a threaded fastener, a rivet fastener, an integrated bolt system, locking pins, fixed fasteners, fixed threaded fasteners, or other structures for permanently attaching the percutaneous post to the overload protection device. As discussed further in this description, the percutaneous post support may also be an attachable and removable system that can be disconnected and re-attached by the amputee. This may include a quick disconnect, a lever and pin system, a tool manipulated disconnect or another type of amputee controllable connect system.

Figure 1B:
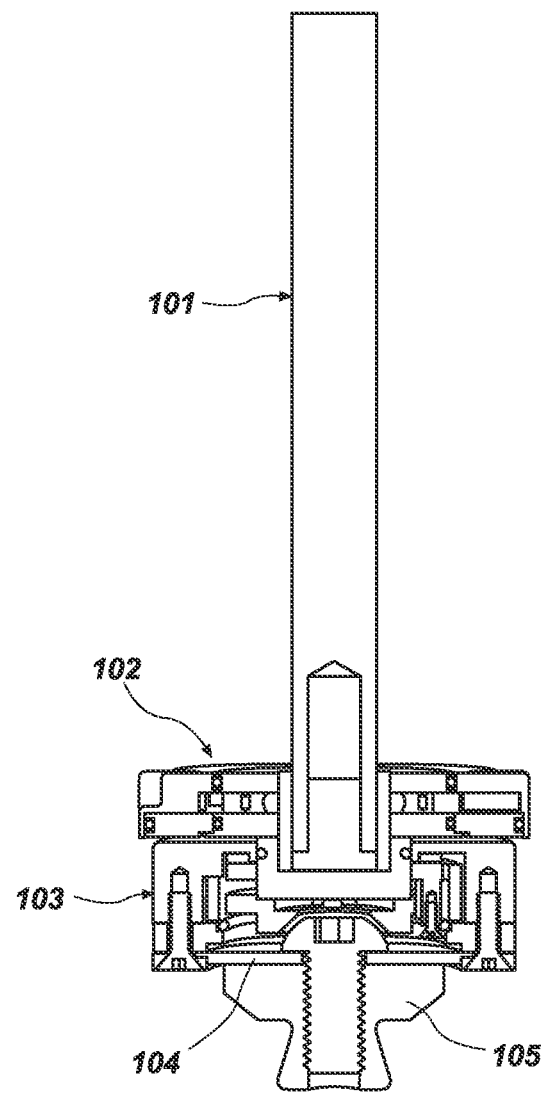
FIG. 1B illustrates an axial cross section of an example of the quick-disconnect and overload protection device.

FIG. 1B illustrates an axial cross section of one example configuration of the quick-disconnect and overload protection device. The percutaneous post support and quick disconnect assembly 102 are illustrated. The torsional resettable overload mechanism 103 is also depicted. The fusible link 104 is illustrated which can provide axial and bending overload protection to a prosthesis user. The fusible link 104 may be "drum-like" because the fusible link is flexible like a drum head but the fusible link may fracture or separate under sufficient load so that the prosthetic limb will separate from the percutaneous post support upon the occurrence of a load that might injure the user and the user's remnant bone. A pyramid attachment 105 may allow for angular alignment of the prosthesis and attachment of a prosthetic hand, hook, tool or a similar type of attachment. In one example, the pyramid attachment 105 may be attached with a threaded fastener. The pyramid attachment may be attached using a pin assembly, nails, bolts, rivets, adhesives, or other attachment assemblies.

The pyramid may be an example of one prosthetic attachment structure but other types of structures or assemblies may be used to attach a prosthetic to the load protection device. For example, a pin system, ratcheting system or other system may be used to connect a prosthetic limb to the load protection device.

Figure 2:
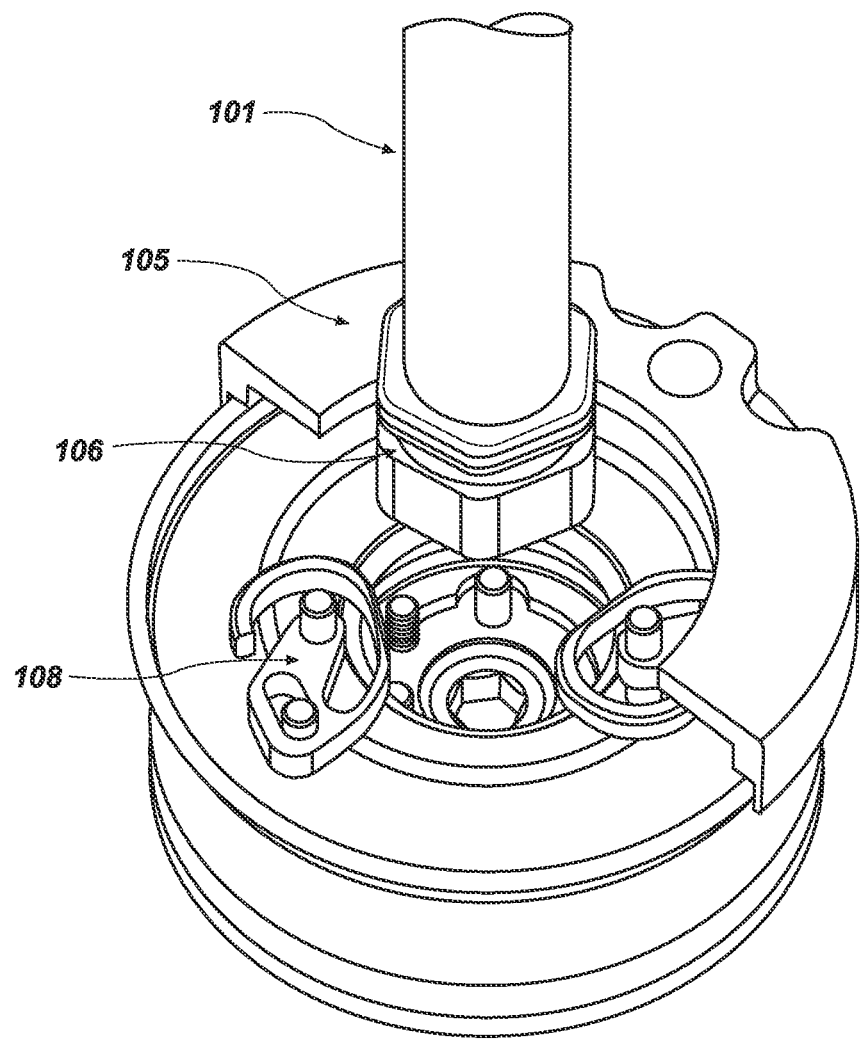
FIG. 2 illustrates an example of a cut away of the top cover that may be rotated clockwise to lock and counter clockwise unlock the prosthesis from a percutaneous post.

FIG. 2 shows a partial cut away of the top cover 105 that may be rotated clockwise to lock and counter clockwise unlock the prosthesis (e.g., a hand or foot prosthesis) from the percutaneous post 101. As the top cover 105 rotates, the top cover 105 engages compliant or spring locking members 108 into a locking groove 106 in one end of the percutaneous post 101. In other configurations, the quick disconnect may be controlled using a lever that moves a blade, or a button can be used to release a blade, ratchet and pawl, pin or similar locking assembly from the percutaneous post. Generally speaking, the quick disconnect may hold the percutaneous post in place with respect to the housing or device in one state, and the quick disconnect may disengage the percutaneous post with respect to the housing or device in a second state.

This quick disconnect system may provide an attachment that minimizes the play or backlash between the quick disconnect system and the percutaneous post 101. The compliant members 108 (e.g., compliant material or spring-loaded cams) may securely engage in a groove 106 on the end of the percutaneous post. When an excessive amount of force is applied to the percutaneous post in the axial direction, the springs provide flexibility to adjust for that force. In some situations, where the axial force is great enough (i.e., a little less force than will injure the amputee), the percutaneous post may dis-engage from quick disconnect system. A pyramid or lock blocks (not seen in FIG. 2 but see FIG. 1) may be used to attach the prosthetic limb to the quick disconnect system, and the lock blocks may be tapered or un-tapered.

Figure 3A:
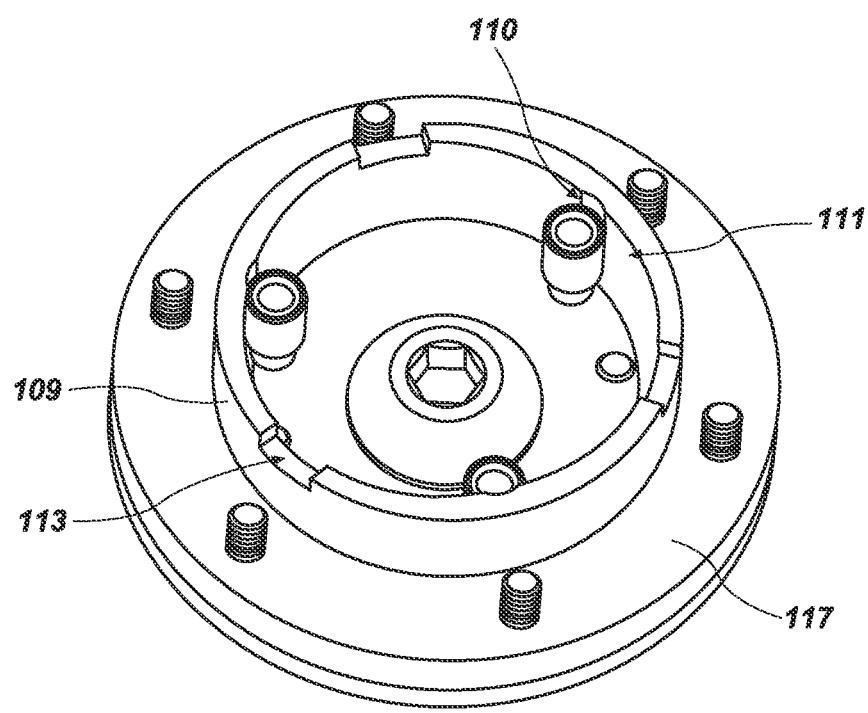
FIG. 3A illustrates an example of a ring-shaped spring with detents and rollers.

FIG. 3A illustrates a ring spring 109 with detents 110 and rollers 111. The ring spring 109 may be secured to the proximal percutaneous post by means of slots and the quick disconnect section of the device. The distal section of the overload protection device may be secured to the prosthesis by means of the pyramid.

The rollers 111 may be attached to the distal section of the device. When the prosthesis is over-loaded in torsion, the prosthesis, distal section of the device, and the rollers rotate when the load is sufficient to distend the ring spring 109 and allow the rollers to roll out of detents 110 (i.e., a roller detent) and roll around the interior surface of the ring spring until another detent is reached. Slots 113 (i.e., spring slots) are cut in the ring spring to enhance the ring's flexibility and/or to assist with attaching to the ring spring 109 to the quick disconnect assembly 102. The ring spring 109 may be attached to the base ring 117 or formed as an integral part of the base ring 117. A ring spring diameter and detents (e.g., detent depths) may be set such that for a desired torsion, the ring spring 109 distends elastically, and the rollers roll or move out of the detents for breakaway protection. The ring spring diameter and detents can also be set to distend elastically to allow for resetting of the rollers in the detents after a breakaway occurs.

In one example of a prosthesis used with this technology, the prosthesis may be a prosthetic hand and/or wrist. In second prosthesis example, the prosthesis may be a foot and/or ankle.

The ring spring 109 or circular spring may also be changed out based on the amount of torsion resistance desired. The ring spring may be removed and replaced with a thinner or thicker ring wall, as desired. A thicker ring spring wall may increase the torsion force for the rollers to breakaway and a thinner ring spring wall can do the opposite. Similarly, the material of the ring spring 109 may be various materials and the material used can affect the flexibility of the ring. For example, the ring may be made of metal, plastic, composite or another suitable spring material.

The resettable torsional over-load protection configuration for the prosthetic attachment device can limit the load moment about the axis of the percutaneous post to prevent injury of the interface to the remnant bone of the prosthesis user. As mentioned before, this load limiting feature is accomplished using a ring spring 109 which has a specified stiffness (e.g., thickness or material type). Furthermore, the ring spring 109 can have one or more detents 110 (e.g. three or five detents) in which rollers 111 are positioned prior to the prosthesis being loaded with torsional loads. When unacceptable torsional loads are applied to the prosthesis, the prosthesis transmits torsional loads to the ring spring 109 through the rollers 111, such that the rollers 111 distend the ring 109 by rolling up the ramp of the detents 110 which may allow the prosthesis to rotate without applying unacceptable torsional loads to the remnant limb.

Rollers 111 that have moved can be reset by the prosthesis user by manually rotating the prosthesis (e.g., an arm, hand or foot) linked to the rollers 111 back into the detents 110. The entry ramp to the detent 110 may be set at an angle that makes resetting comparatively easy.

Figure 3B:
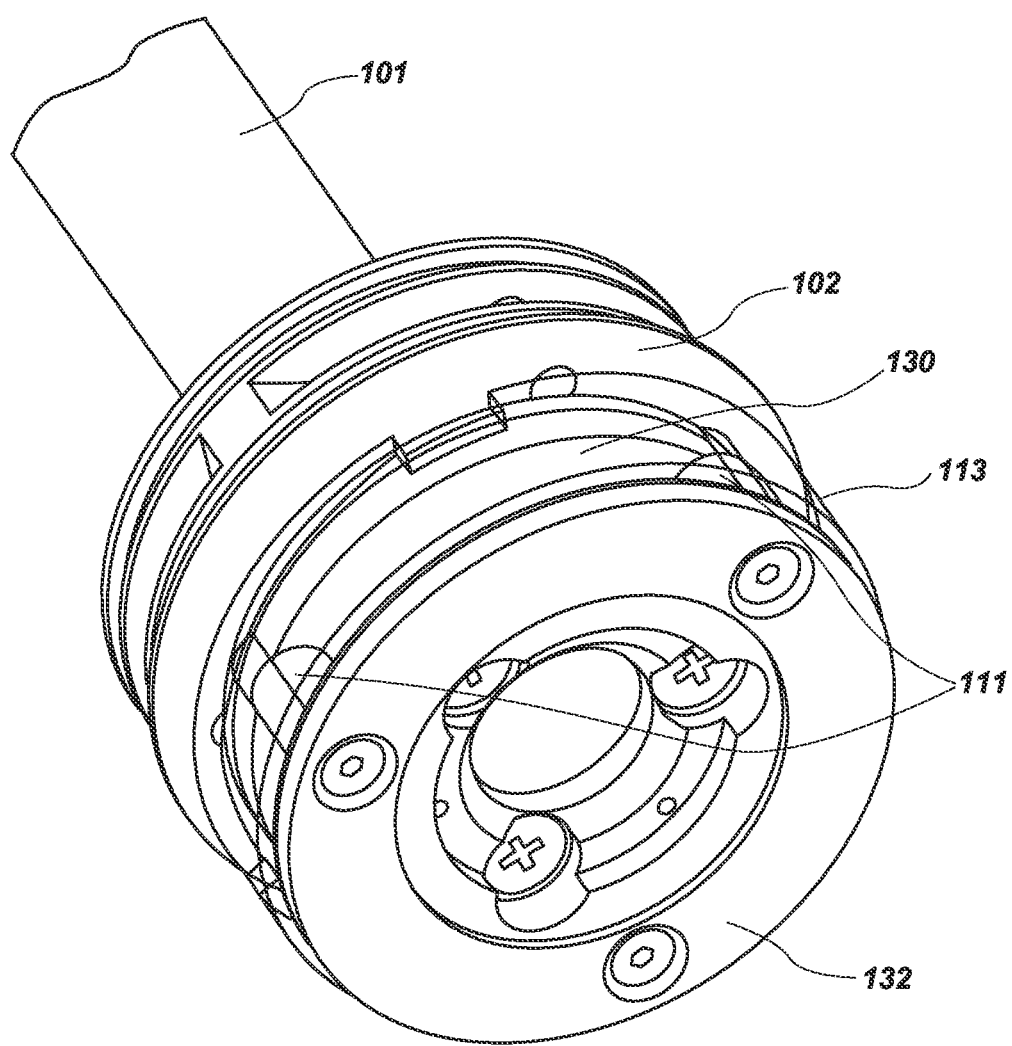
FIG. 3B illustrates an example perspective cut away view showing the rollers and a carousel for the rollers.

FIG. 3B illustrates an example perspective cut away view of the overload protection device depicting the rollers 111 and a carousel for the rollers 111. The carousel has first carousel plate 130 or first roller support and a second carousel plate 132 or second roller support. The carousel and carousel plates are attached (e.g., rigidly) to the quick release housing 102 or quick disconnect. Thus, the carousel is directly attached to the quick release housing 102. When a load is applied to the prosthesis, the load transfers from the prosthesis to the base of the torsional overload protect and to the ring spring 113 (which is transparent in this figure). The rollers 111 may act on the ring spring 113 and the ring spring 113 can distend to breakaway. The post 101, carousel and carousel plates 130, 132, and rollers 111 act as a stationary ground for the breakaway system. The retaining plate 117 (See FIG. 1) may act as the second carousel plate 132 or the retaining plate 117 may be mounted over the second carousel plate 132.

Figure 4:
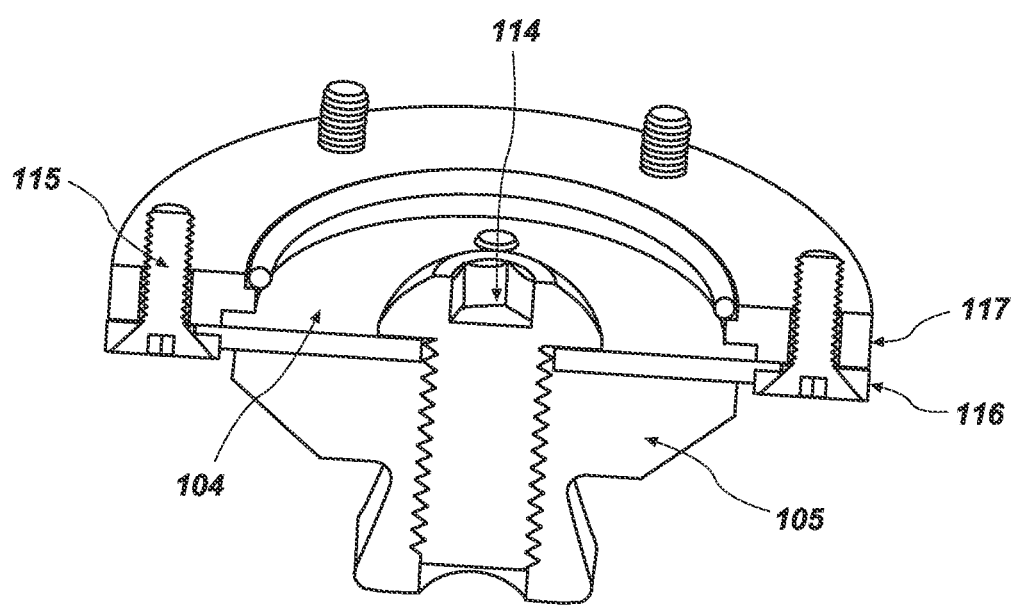
FIG. 4 illustrates an example of a fusible link secured to a pyramid by a screw.

FIG. 4 shows the fusible link 104 secured to pyramid 105 by means of a threaded screw 114. The fusible link 104 may be considered drum-like where the fusible link 104 may be flexible like a drum head but the fusible link may breakaway under sufficient load. A pyramid 105 can be securely attached to the prosthesis. The fusible link 104 may be attached to the body or housing of the prosthetic attachment device by means of screws 115 between a retaining plate 116 and base ring 117. The fusible link 104 can be designed to protect the percutaneous post and remnant limb from axial and bending overloads.

Referring further to FIG. 4, the fusible link 104 in the prosthetic attachment device is designed to break away when axial or bending loads are applied to the prosthesis that could harm the percutaneous post interface for the remnant bone of the prosthesis user. The fusible link 104 may break along a circumference of the fusible link 104, or the fusible link 104 may break in the center of the fusible link 104 where the bolt 114 passes through the fusible link 104. Other types of scoring may be applied to the fusible link 104 to encourage the fusible link 104 to breakaway in defined patterns or at defined force loads.

The fusible link 104 can provide a compact form of bending overload protection. This is valuable because a prosthetic limb may be desired to fit within the envelope of a human limb as defined prior to limb loss. The fusible link 104 can provide bending overload protection without adding undue length to the prosthesis and enables the prosthetic to better fit within the desired hand, wrist and arm envelope.

The fusible link 104 may also be considered a membrane with breakaway properties. The fusible link 104 can be replaced when a breakaway event occurs. Replacing the fusible link 104 is straightforward using hand tools to remove and replace the screws or fasteners (e.g., threaded fasteners).

The fusible link 104 can also be tuned for specific loads. The breakaway performance of the fusible link 104 may be changed by varying the material thickness. For example, the material may be metal, plastic, composite material, or other combinations of material. The fusible link 104 also provides more reproducible results in terms of a consistent amount of torque that will cause the fusible link 104 to breakaway. In contrast, elastomeric materials are more difficult to tune and estimate provided protection as defined by precise weights, thicknesses and strengths. The fusible link 104 provides a more consistent and reproducible protection mechanism than elastomeric or similar materials.

Since the fusible link creates only small variations in the breakaway force need to breakaway the fusible link, then a prosthetist can better determine which materials may work well for an amputee. This may mean that each patient can have a different breakaway strength or force threshold selected for them individually. The prosthetist can install different membranes for different patients or user based on the amount of remnant bone, patient's weight, patient's height, activity level, etc. If the fusible link 104 breaks or fails, then the fusible link 104 can be replaced by the patient or the prosthetist.

The fusible link 104 may also be able to flex, giving the remnant limb a level of shock absorption and a natural level of compliance. The fusible link 104 may be made from a plastic, composite material, fiberglass or other flexible material. When an axial load is applied to the prosthetic limb, loads are coupled to the fusible link 104. If the axial load exceeds the acceptable load, then the bolt 114 that extends through the center of the "drum-like" member 104 can transfer the forces to the fusible link 104 until the resultant stresses exceed the strength of the material and the fusible link 104 ruptures.

To reiterate, when a bending load is applied to the prosthetic limb, a moment transverse to the axis of the prosthetic attachment device may be applied to bolt 114. The bolt 114 in turn applies a load to the "drum-like" fusible link 104. The fusible link 114 is designed to exhibit a level of compliance that absorbs shock loads to the prosthesis. When bending loads applied to the prostheses exceed acceptable bending loads, the fusible link is designed to break. In addition, the fusible link system is designed to be replaceable.

The present technology provides a device for protecting an osseointegrated percutaneous post from overload forces by using a spring-loaded "drum-like" fusible link. Furthermore the "drum-like" fusible link may be clamped at the center of the membrane or drum membrane. Loads are transmitted to the percutaneous post through the membrane and the membrane can break away when overloaded, thereby protecting the osseointegrated percutaneous post interface with the intact human bone.

The "drum-like" fusible link can have two or more membranes that are used together by layering or joining the membranes together. If one membrane fails by fracturing, then the second membrane can fail plastically such that that the membrane that fails plastically acts like a tether to secure the limb from disconnecting from the prosthesis user.

The "drum-like" fusible link may have the membrane clamped such that an overload produces primarily shear loads on the membrane. Alternatively, the "drum-like" fusible link may have the membrane clamped such that the clamp slips when torsionally loaded to protect for torsional overloads. For example, the clamping may only be tight enough to resist torsion up to certain force threshold, at which point the fusible link may slip torsionally. Further, the "drum-like" fusible link may have the membrane clamped such that when a bending load is applied, the membrane fractures in shear in the direction of bending and deforms plastically ninety degrees from the direction of bending to secure that limb from disconnecting from the prosthesis user.

While FIGS. 1A-5 have illustrated this technology with both the fusible link and a ring spring with rollers, a prosthetic limb may use either structure separately. For example, a prosthetist may prescribe a fusible link for a prosthetic limb of a first patient that may allow for bending overload protection without the ring spring and rollers. A prosthetist may determine that a second patient needs the ring spring with a roller for torsional load protection but this second patient does not need the fusible link. The structure selected may depend on the needs of each amputee (e.g., the varying bone support for an implant in the amputee).

O-rings or flat seals may be used at part or element interfaces to protect the overall device from water and dirt damage. For example O-rings may be used between any of surfaces joining at least two of: the fusible link, base ring, spring ring, fastener, housing structures, or quick disconnect.

As discussed earlier, length, size and weight are very important for upper limb prosthetics. This technology does not add significant length to a prosthetic but can provide full functionality and torsion protection to an amputee.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The invention claimed is:

1. A device for protecting a percutaneous post that is osseointegrated in a human limb, comprising:
 a housing having a first end and a second end;
 a quick disconnect coupled to the first end of the housing to removably support the percutaneous post;
 a base ring attached to the second end of the housing;
 a fusible link coupled to the base ring, wherein the fusible link is a membrane; and
 a fastener coupled to the fusible link to enable fastening of the fusible link to a prosthesis.

2. The device of claim 1, wherein the quick disconnect is controlled using at least one of a lever, spring locking members, or a button.

3. The device of claim 2, wherein the quick disconnect retains the percutaneous post in place with respect to the housing in one state and does not retain the percutaneous post with respect to the housing in a second state.

4. The device of claim 3, wherein the fusible link is configured to breakaway when overloaded to protect an interface of the percutaneous post with a human bone.

5. The device of claim 1 wherein a pyramid attachment is held by the fastener to a center of the fusible link.

6. The device of claim 1, wherein the base ring is attached to a ring spring, which are both connected to the second end of the housing through a roller or rollers.

7. The device of claim 6, wherein the ring spring has a detent or detents for the rollers.

8. The device of claim 7, wherein a ring spring diameter and detents are set such that for a desired torsion, the ring spring distends elastically and the roller or rollers roll out of the detents for breakaway protection.

9. The device of claim 8, wherein the ring spring diameter and detent or detents are set to distend elastically to allow for resetting of the rollers after breakaway.

10. The device of claim 1, wherein the fusible link is clamped such that an overload produces primarily shear loads on the fusible link.

11. The device of claim 1, wherein the fusible link is clamped such that the fusible link slips when torsionally loaded to protect for torsional overloads.

12. The device of claim 1, wherein the fusible link is clamped such that when loaded with a bending load the fusible link fractures in shear in a direction of bending and plastically at ninety degrees from the direction of bending to secure a prosthetic attachment from disconnecting from a prosthesis user.

13. The device of claim 1, wherein a prosthetic attachment structure is a pyramid attachment.

14. A device for protecting an osseointegrated percutaneous post in a human limb from overloading when connected to a prosthesis, comprising:
   a housing having a first end and a second end;
   a percutaneous post support coupled to the first end of the housing to support the osseointegrated percutaneous post;
   a base ring attached to the second end of the housing;
   a fusible link attached to the base ring, wherein the fusible link is a membrane; and
   a fastener coupled to the fusible link to enable fastening of the fusible link to a prosthetic attachment structure.

15. The device of claim 14, wherein a pyramid attachment is held by the fastener to a center of the fusible link.

16. The device of claim 14, wherein the fusible link is configured to breakaway when overloaded to protect an interface of the percutaneous post with a human bone.

* * * * *